United States Patent [19]
Keen et al.

[11] Patent Number: 5,931,788
[45] Date of Patent: Aug. 3, 1999

[54] METHOD AND APPARATUS FOR IMAGING INTERNAL ORGANS AND VASCULAR STRUCTURES THROUGH THE GASTROINTESTINAL WALL

[76] Inventors: Richard R. Keen, 1 Enclave Ct., Burr Ridge, Ill. 60521-6300; Leon J. Frazin, 542 Willgate Terrace, Glencoe, Ill. 60022

[21] Appl. No.: 08/985,610

[22] Filed: Dec. 5, 1997

[51] Int. Cl.$^6$ .................................. A61B 8/12; A61B 8/00
[52] U.S. Cl. ........................... 600/462; 600/117; 600/459
[58] Field of Search .................................. 600/439, 463, 600/437, 114, 462, 117

[56] References Cited

U.S. PATENT DOCUMENTS

| | | | |
|---|---|---|---|
| 4,327,738 | 5/1982 | Green et al. | 600/109 |
| 4,344,159 | 8/1982 | Ballinger . | |
| 4,349,032 | 9/1982 | Koyata | 600/462 |
| 4,375,818 | 3/1983 | Suwaki et al. . | |
| 4,582,067 | 4/1986 | Silverstein et al. . | |
| 4,819,650 | 4/1989 | Goldstein . | |
| 5,022,399 | 6/1991 | Biegeleisen . | |
| 5,025,778 | 6/1991 | Silverstein et al. . | |
| 5,038,789 | 8/1991 | Frazin . | |
| 5,054,491 | 10/1991 | Saito et al. . | |
| 5,081,993 | 1/1992 | Kitney et al. . | |
| 5,178,150 | 1/1993 | Silverstein et al. . | |
| 5,190,045 | 3/1993 | Frazin . | |
| 5,207,225 | 5/1993 | Oaks et al. . | |
| 5,220,924 | 6/1993 | Frazin . | |
| 5,390,661 | 2/1995 | Griffith et al. | 600/114 |
| 5,394,848 | 3/1995 | Frazin et al. | 600/462 |
| 5,394,878 | 3/1995 | Frazin . | |
| 5,469,853 | 11/1995 | Law et al. . | |
| 5,492,126 | 2/1996 | Hennige et al. . | |
| 5,671,748 | 9/1997 | Itoi | 600/462 |

OTHER PUBLICATIONS

Frazin, L., Keen, R., "A Method for Transgastric Abdominal Vascular Ultrasound", *ASAIO Journal*, Mar.–Apr., 1997 issue, vol. 43, No. 2, p. 21.

Keen, R., Yao, J., Astleford, P., Blackburn, D., Frazin, L., "Feasibilty of Transgastric Ultrasonography of the Abdominal Aorta", *Journal of Vascular Surgery*, vol. 24, No. 5, pp. 834–842.

*Primary Examiner*—Marvin M. Lateef
*Assistant Examiner*—Ali M. Imam
*Attorney, Agent, or Firm*—Banner & Witcoff, Ltd.

[57] ABSTRACT

The present invention is a method and apparatus for ultrasound imaging of internal structures near a stomach of a patient. Under the present invention, high resolution images of abdominal structures may be obtained including, for example, the abdominal aorta, kidneys, the liver, superior mesenteric, both renal arteries, the hepatic arteries, the splenic artery, the vena cava, renal veins, portal vein, splenic and mesenteric veins. High resolution imaging of blood flow within blood vessels including those within organs may also be obtained. High-resolution imaging of these structures thereby obviates the need for otherwise invasive procedures. The imaging device of the present invention includes a probe having a head, a body and an end opposite the head. An ultrasonic transducer is coupled to the head of the probe and a gel material covers the ultrasonic transducer to enable a good contact with a stomach wall portion. The imaging device has a substantially rigid body through the use of a substantially rigid sheath or a sheath and a substantially rigid rod. The imaging device also includes a handle near the end of the probe for manipulating the location and positioning of the ultrasonic transducer to ultrasonically image the tissue and/or organ of interest.

48 Claims, 4 Drawing Sheets

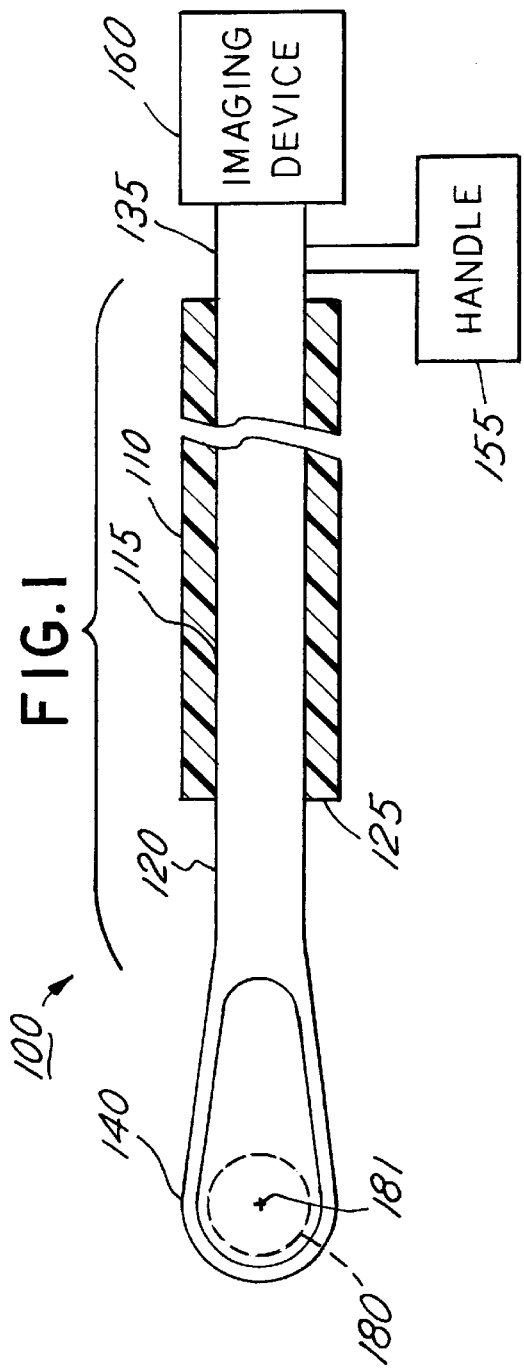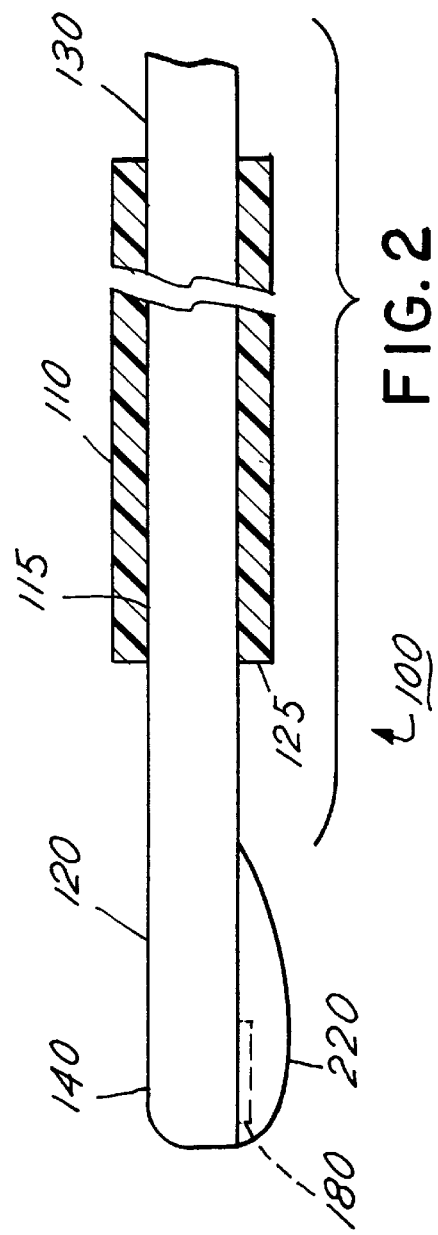

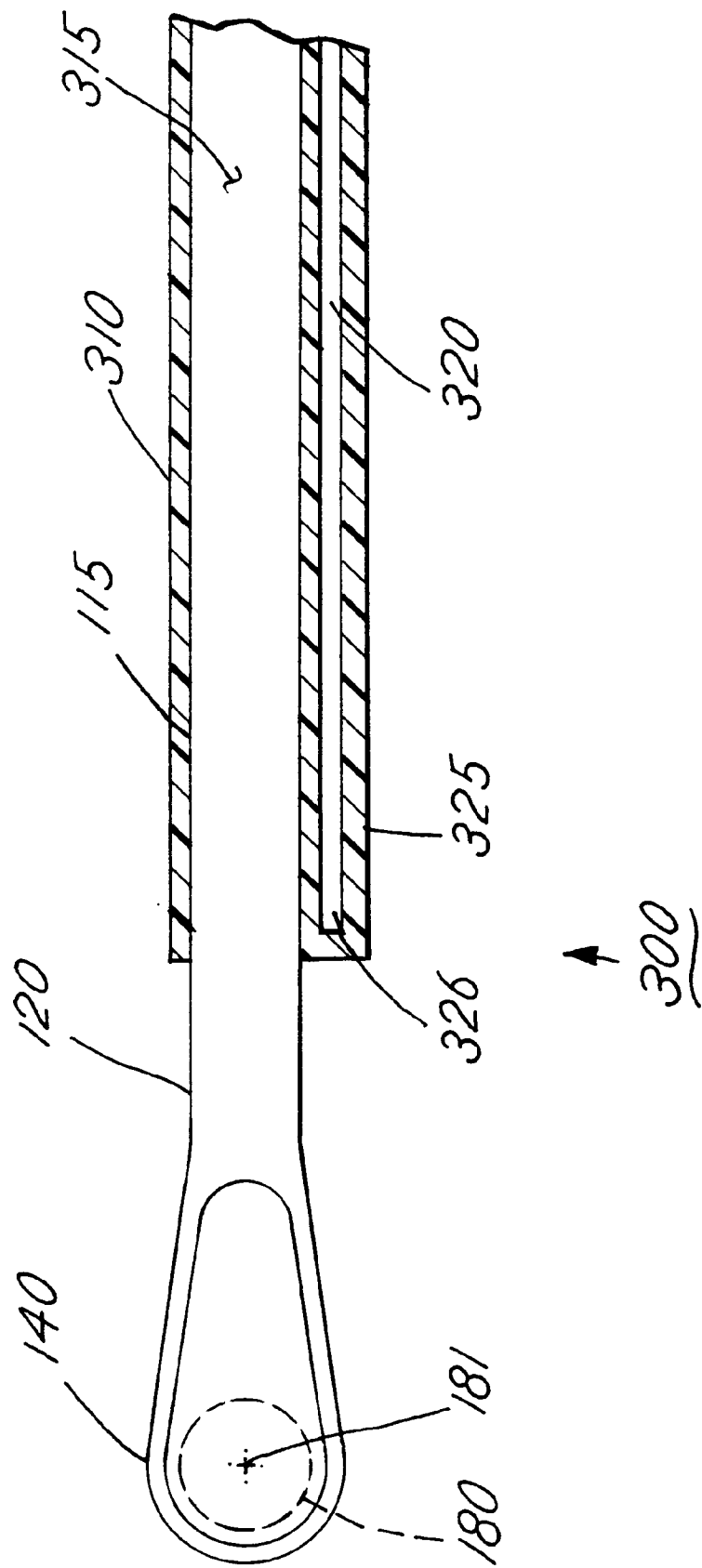

METHOD AND APPARATUS FOR IMAGING INTERNAL ORGANS AND VASCULAR STRUCTURES THROUGH THE GASTROINTESTINAL WALL

BACKGROUND OF THE INVENTION

1. Field of the Invention

The present invention relates to ultrasound imaging, and more particularly to techniques for ultrasound imaging of internal organs and vascular structures via the gastrointestinal wall.

2. Description of the Related Art

In recent years ultrasound imaging techniques have significantly developed, particularly where images of internal structures lying deep within the patient are desired through the use of non-invasive, non-surgical procedures. Cardiac imaging of organs near the esophagus is achieved using an ultrasonic transducer attached to a probe which is inserted into the mouth of a patient and placed against the interior wall of the esophagus near the internal organ or structure of interest. Cardiac imaging has often been achieved through the use of transesophageal ecocardiography (TEE). The proximity of the esophageal transducer to the image structures allows the use of resolution enhancing higher frequency transducers. However, adequate visualization of the abdominal aorta, its branches and other organs and structures in the abdominal area is not possible through the use of TEE. The TEE transducer falls away from the posterior wall of the stomach once it leaves the esophagus and enters the gastric cardia, where interposed air prevents imaging of the abdominal vascular structures.

It is often desirable to obtain high resolution imaging of the internal structures and organs in the abdominal area through the use of non-invasive, non-surgical procedures. One such application is monitoring of blood flow to the kidney through ultrasonic imaging. Loss of blood flow to the kidney is a common cause of kidney failure requiring patient dependency on hemodialysis. No known technique presently exists to reliably monitor blood flow to the kidney through minimally-invasive means. If such low blood flow is detected, intervention may be possible to prevent kidney failure. Another application is imaging of the vena cava which may be useful when filters are implanted in the vena cava to trap blood clots. Under present techniques, implantation of filters in the vena cava requires the use of dyes and x-rays.

Invasive surgery is generally required to obtain sufficiently detailed and clear images of internal organs and structures near the stomach. Three-dimensional CT scanning and magnetic resonance angiography have the potential to fulfill this imaging need, but these technologies have yet to be fully developed. Transabdominal duplex scanning is yet another procedure for evaluating the abdominal organs and structures of the patient, particularly the abdominal aorta and its major branch vessels for the presence of significant atherosclerotic disease. However, major limitations prevent a more widespread application of this technique. For example, for length of time required to perform a complete vascular duplex examination of the abdominal aorta, celiac access, superior mesenteric, and both renal arteries can exceed one hour, even when the examination is performed by experienced vascular technologists. In addition, this technique requires the use of lower frequency transducers (less than 5 MHZ) to traverse this distance. The depth of structures to be imaged and the use of low frequency transducers may result in poor resolution and image quality. Intestinal gas and abdominal wall fat may also limit the resolution and amount of information obtained during transabdominal vascular ultrasound imaging.

U.S. Pat. No. 5,394,878 entitled "Method for Two Dimensional Real Time Color Doppler Ultrasound Imaging Of Bodily Structures Through The Gastro Intestinal Wall", issued on Mar. 7, 1995, discloses a method for two dimensional real time color Doppler ultrasound imaging of bodily structures through the gastrointestinal wall. This patent discloses imaging of deep internal organs and vascular structures by introduction of a transducer on the end of a probe into either the colon or the esophagus of a patient. The transducer can then be positioned adjacent to the organ or vessel of interest for ultrasonic imaging. U.S. Pat. No. 5,492,126 entitled "Probe For Medical Imaging And Therapy Using Ultrasound", issued Feb. 20, 1996, also discloses a probe for inspecting an internal organ of a patient. The patent discloses a probe having a flexible portion at a distal end of the probe.

However, these inventions are unable to obtain the level of ultrasonic imaging resolution required to adequately diagnose or observe conditions of the internal structures or organs of interest. While these probes can be guided into either the colon or the esophagus of the patient, they cannot be positioned to desired locations near the wall of the stomach to adequately obtain clear and detailed ultrasound images of certain organs or vessels. Particularly, bending of the probe along the entire length of the body prevents the transducer from avoiding intervening gases which is necessary to obtain high resolution images. Imaging of abdominal organs and structures, for example the abdominal aorta, kidneys, superior mesenteric, both renal arteries and the vena cava, is limiting under known techniques. Imaging of blood flow within blood vessels in the abdominal region is also limiting under known techniques.

A flexure control mechanism such as those found in endoscopes may be used to control the bending of the probe near the ultrasonic transducer. Such a concept has been disclosed in U.S. Pat. No. 5,492,126 entitled "Probe For Medical Imaging and Therapy Using Ultrasound", issued in Feb. 20, 1996. However, such flexure control is still unable to obtain the level of precise positioning required to adequately image certain internal organs and structures.

SUMMARY OF THE INVENTION

The present invention provides a method and apparatus for obtaining high resolution imaging of internal structures and organs in the abdominal area through non-invasive or minimally invasive procedures. In one embodiment, the invention includes a probe having a head, body and end, an ultrasonic transducer positioned near the head of the probe, a gel material covering the ultrasonic transducer, a handle at the end of the probe for positioning of the ultrasonic transducer, and a substantially rigid sheath along the body of the probe. The invention thereby allows positioning of the probe against the interior wall of the stomach to obtain clear and detailed images of desired structures in the abdominal region. Blood flow within abdominal blood vessels may also be monitored. The sheath allows for improved positioning of the ultrasonic transducer over techniques known in the prior art. The sheath may be permanently connected to the probe or may be a removable sheath. In another embodiment, the substantially rigid sheath is a flexible sheath having a cavity for insertion of a substantially rigid rod. In yet another embodiment, the sheath may be a flexible material which becomes substantially rigid at body temperature. In still another embodiment, the flexible body of the probe is made substantially rigid by tightening of internal cables.

By introducing the ultrasonic transducer into the stomach of a patient, the ultrasonic transducer may be accurately positioned to be in association with a portion of the internal wall of the stomach adjacent to the desired internal structure to be imaged. The probe of the present invention may also enable displacement of the gastrointestinal wall to areas near the stomach which are not directly adjacent to the stomach thereby allowing high-resolution imaging of a greater portion of the abdominal area. The sheath allows for improved positioning of the ultrasonic transducer over techniques known in the prior art. The sheath also allows the stomach to be displaced in multiple directions to be in closer relationship with abdominal organs or structures of interest. By minimizing the distance between the head of the probe and the desired imaging structure, higher frequency (greater than 5 MHZ) transducers may be used. The present invention provides high resolution imaging of abdominal structures not otherwise attainable under known techniques; these structures include, but are not limited to, the abdominal aorta, the celiac, the hepatic, the splenic, the superior mesenteric, the right and left renal arteries, the entire length of the intra-abdominal vena cava, retro-hepatic vena cava, renal veins, mesenteric veins, portal veins, and hepatic veins. The gel material provides an improved contact between the ultrasonic transducer and the interior wall of the stomach. In another embodiment the gel material may be instead a liquid material which is filled inside a blow-up stand-off around the ultrasonic transducer.

These as well as other novel advantages, details, embodiments, features and objects of the present invention will be apparent to those skilled in the art from following the detailed description of the invention, the attached claims and accompanying drawings, listed herein, which are useful in explaining the invention.

BRIEF DESCRIPTION OF THE DRAWINGS

In the following text and drawings, wherein similar reference numerals denote similar elements throughout the several views thereof, the present invention is explained with reference to illustrative embodiments, in which:

FIG. 1 is a cross-sectional front view of one embodiment of the imaging device of the present invention;

FIG. 2 is cross-sectional top view of the head portion of the ultrasonic transducer of FIG. 1;

FIG. 3 is a cross-sectional view of another embodiment of the imaging device of the present invention;

DETAILED DESCRIPTION OF THE PREFERRED EMBODIMENT

Figure 4:
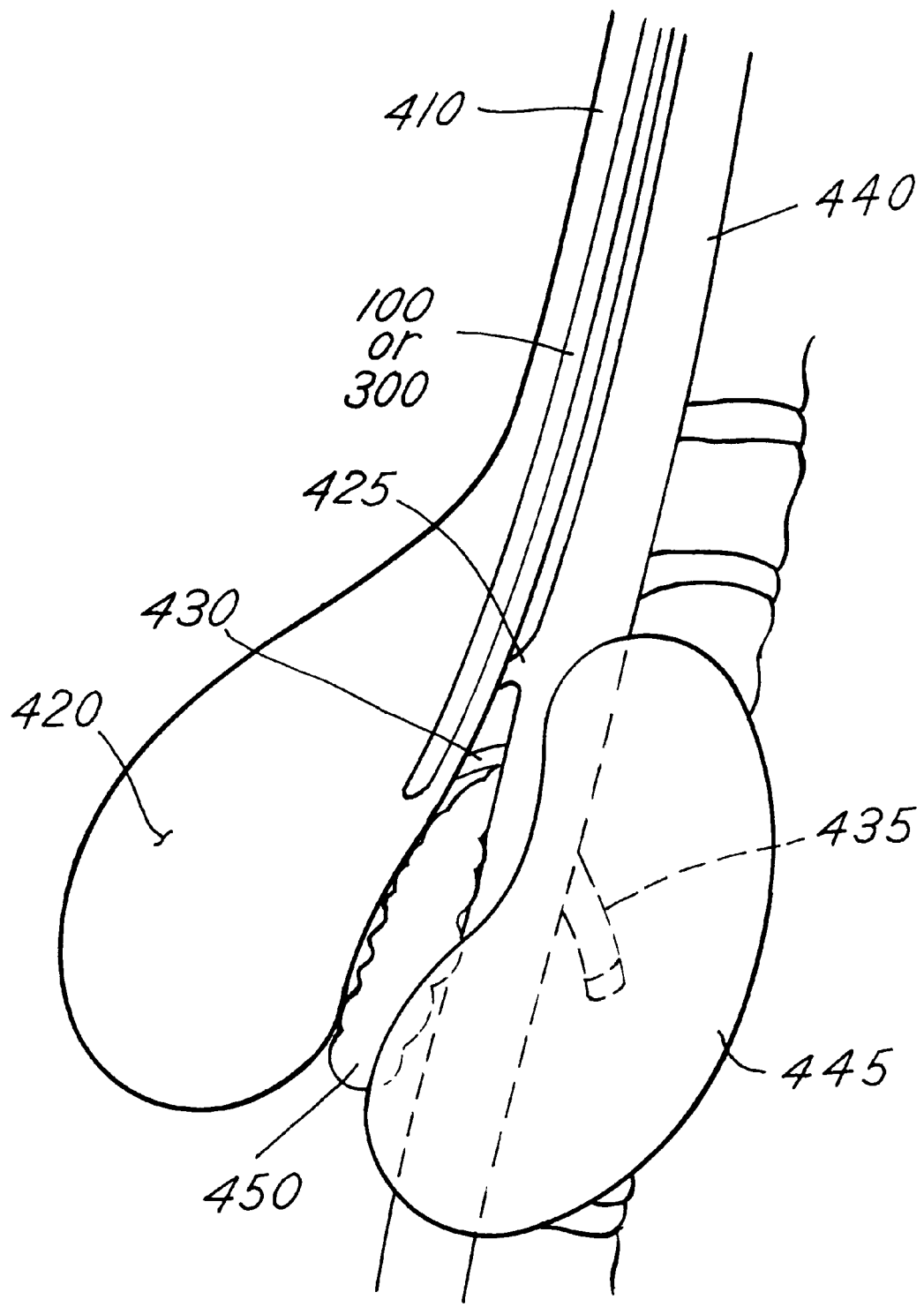
FIG. 4 is an anatomical drawing depicting the insertion of the imaging device into the stomach of a patient.

For a better understanding of the present invention, reference may be had to the following detailed description taken in conjunction with the appended claims and accompanying drawings.

FIG. 1 is a cross-sectional view of an imaging device 100 in accordance with one embodiment of the present invention. The imaging device 100 consists of a probe 120 having a head 140, a body 115, an end 135, and a sheath 110. The probe 120 is connected to an imaging display device 160 at the end 135 of the probe 120. An ultrasonic transducer 180 is attached near the head 140 of the probe 120 in a direction substantially perpendicular to the axis of the head 140. As shown in FIG. 2, a cross-sectional top view of the head portion of the ultrasonic transducer of FIG. 1, gel material 220 is attached to the head 140 and covers the ultrasonic transducer 180. Gel material 220 provides improved contact of the transducer 180 with the interior wall of the stomach by preventing intervention of gaseous matter. Those skilled in the art will appreciate that gel material 220 may be any ultrasound gel or any liquid material that serves the purpose of providing a good contact between the transducer 180 and the interior wall of the stomach. For example, gel material 220 may instead be a liquid material that fills a blow-up standoff. Those skilled in the art will also appreciate that other techniques or materials may be utilized to prevent intervention of gaseous matter between the transducer 180 and the internal wall of the stomach. The imaging device 100 may have a cover (not shown) consisting of a balloon or condom material. When the probe 120 is inserted into the stomach of the patient, the cover thereby provides a sterile barrier between the patient and the imaging device 100.

Referring back to FIG. 1, the imaging device 100 further includes a substantially rigid sheath 110 which is placed over the body 115 of the probe 120. The substantially rigid sheath 110 prevents the body 115 of the probe 120 from bending as the probe 120 is being manipulated and positioned. Sheath 110 may be a plastic material or of any other material having a substantially rigid resiliency. Although not required, the sheath 110 may be in rigid or semi-rigid contact with the body 115 of the probe 120 to avoid or minimize any slippage. Head 140 of the probe 120 extends outside of the sheath 110 to allow the head 140 to bend and position the transducer 180 to desired locations. The center 181 of the ultrasonic transducer 180 may be in the range of 1 centimeters (cm) to 10 cm from the end 125 of the sheath 110 and preferably in the range of 5.5 cm. This allows adequate bending of the head 140 while maintaining a substantially rigid probe 120 along the body 115. The probe 120 also has a handle 155 coupled near the end 135 of the probe 120 for use by a surgeon to manipulate the location of the probe's head 140 and to position the ultrasonic transducer 180 against the interior wall of the stomach for ultrasonic imaging of tissue and/or organs of interest. Once the head 140 is positioned, the head 140 may be locked in place with a locking mechanism such as, for example, an external switch which tightens an internal cable to the head 140 (not shown). Such a locking mechanism may be one similar to those commonly used in endoscopes. The locking mechanism is commonly used on endoscopes and transesophageal ultrasound transducers routinely only make the probe's head 140 stiff, leaving the body 115 flexible. In another embodiment, the present invention includes one or more internal cables to the body 115 of the probe 120 which are controlled by external switches at the handle 115. The switches tighten these internal cables thereby making the body 115 stiff once the head 140 is positioned. One set of internal cables would permit tightening, locking, positioning and making inflexible the entire probe 120 including its end 135, body 115 and head 140. Either the head 140 or the body 115 could be made flexible or substantially rigid independent of each other or simultaneously with these internal cables extend switches and locking mechanisms.

FIG. 3 is a sectional view of another embodiment of an imaging device 300 of the present invention. In this embodiment, probe 120 is covered by a sheath 310. Unlike the embodiment of imaging device 100, sheath 310 does not have a substantially rigid portion. Sheath 310 contains a first cavity 315 in which probe 120 may be inserted. First cavity 315 is open at both ends to allow insertion and protrusion of probe 120 as it is inserted in the sheath 310. Sheath 310 also has a second cavity 320 for insertion of a substantially rigid rod 325. When inserted, the end 326 of the rod 325 may be in the range of 1 cm to 10 cm from the center 181 of the ultrasound transducer 180 and preferably in the range of 5.5 cm. Under this embodiment, the flexible probe 120 may be inserted into the mouth and down the esophagus of a patient and when the probe 120 has entered the stomach, rod 325 may thereafter be inserted into the second cavity 320 of sheath 310, thereby making the body 115 of the probe 120 substantially rigid.

The probe 120 and sheath 110 or 310 may be a single assembly or may be detachable units so that the probe 120 may be used for other applications. Other mechanisms are also conceivable under the present invention for maintaining a substantially rigid body 115 of the probe 120. For example, rod 325 of FIG. 3 may be of a material that is flexible at room temperature which becomes substantially rigid at 99.6° F. or higher. Such a material may be an alloy, for example, nitinol. Under this embodiment, probe 120 may be easily inserted while it is flexible. This reduces any gagging reflex that the patient may have if the patient is conscious during the procedure. Upon insertion of the probe 120, the rod 325 will become substantially rigid once it has reached the temperature of the patient's body. The substantially rigid body 115 of the probe 120 thereby allows adequate positioning of the ultrasound transducer 180 within the stomach. In another example, sheath 310 of FIG. 3 may have only a single cavity, and the rod 325 may be inserted within the same cavity as that for the probe 120 or the rod 325. Alternatively, the probe 120 may have a cavity (not shown) located within the probe 120 such that the rod 325 may be inserted within the cavity within the probe 120 itself. In this embodiment of the probe 120, the sheath 310 would not be required.

FIG. 4 is an anatomical drawing showing the insertion of the imaging device 100 or 300 into the stomach 420 of a patient. The imaging device 100 or 300 is inserted through the esophagus 410 of the patient until the head 140 reaches the stomach 420 of the patient. Sheath 110 or 310 is positioned mainly in the esophagus 410. The head 140 may be positioned in good contact with an internal wall portion of the stomach 420. Internal structures in the abdominal area, particularly organs and blood vessels located behind the stomach, may thereby be viewed. Blood vessels include, for example, the celiac 425, the superior mesenteric 430, the left renal 435, the right renal (not shown), the abdominal aorta 440 and paired venus structures (not shown). Abdominal organs include, for example, the kidneys 445 and the pancreas 450 and the liver (not shown). Those skilled in the art will appreciate that other abdominal structures may also be viewed under the present invention.

Figure 5:
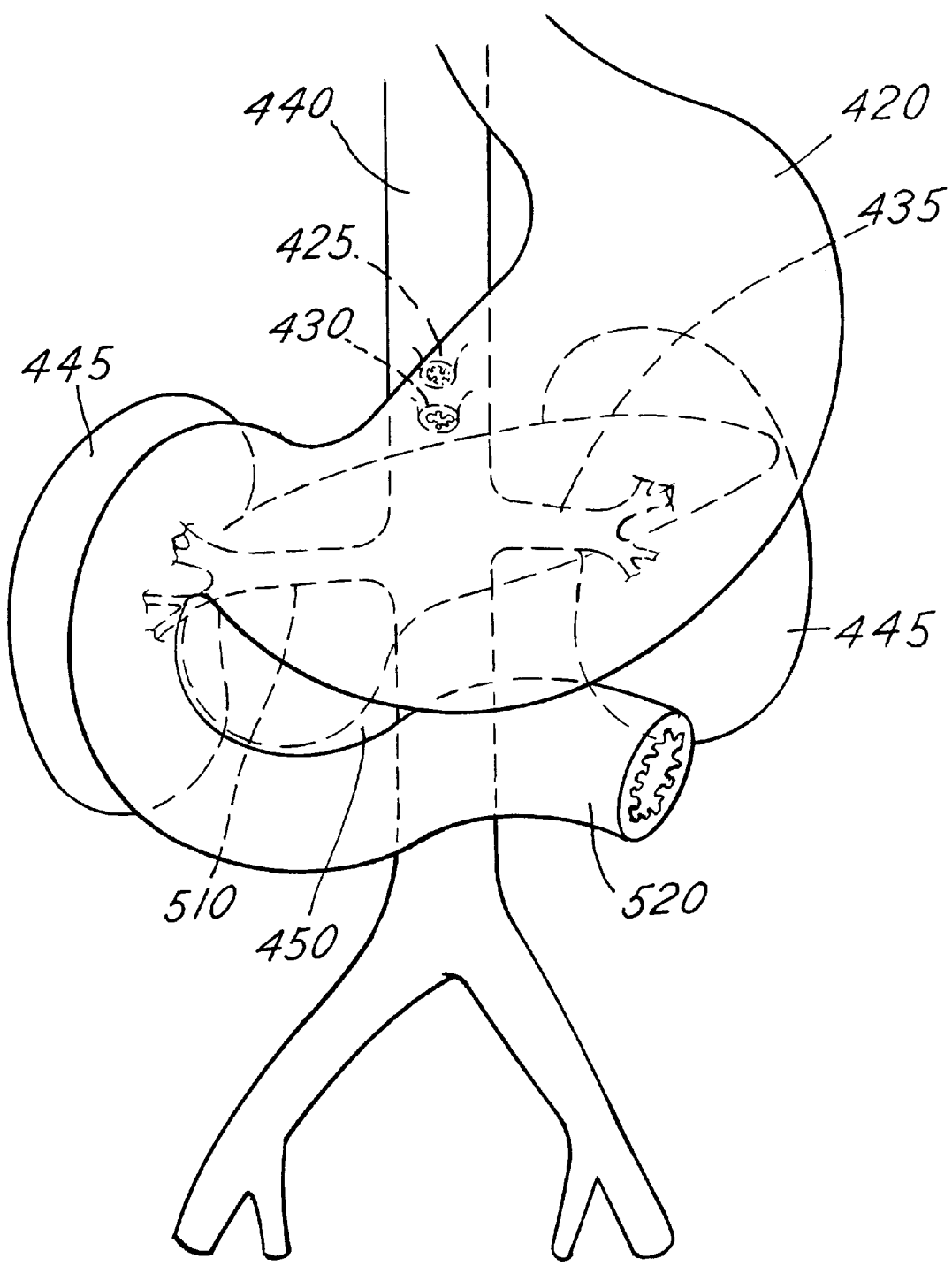
FIG. 5 is an anatomical view describing the location of certain internal structures relative to the esophagus, stomach, and duodenum.

FIG. 5 is an anatomical view of certain internal structures showing the relative location of these structures to the esophagus 410, stomach 420, and duodenum 520. The celiac 425, the superior mesenteric 430, the right renal 510, the left renal 435, the kidneys 445 and the pancreas 450 may be viewed through the stomach. Although not shown in the figure, other structures and blood vessels in the abdominal area may also be viewed including, for example, the vena cava, retro-hepatic vena cava, and other hepatic, portal and renal veins. The probe 120 may also displace the stomach in any direction to achieve closer positioning of the transducer 180 relative to the desired structure of interest. For example the probe 120 may displace the stomach such that lower portions of the abdominal aorta may be viewed.

In one embodiment, the transducer 180 operates in a Doppler mode to allow adequate imaging of blood vessels and the flow of blood within. In another embodiment, the transducer 180 operates in a B-mode to allow high resolution imaging of internal organs in the abdominal area. The transducer 180 and probe 120 devices may be, for example, an Omniplane II Transducer sold by Hewlett-Packard Company, although any type of ultrasound and probe devices may be implemented.

The imaging devices 100 and 300 may be utilized to obtain high resolution ($\geq 5$ MHZ) imaging of the blood flow to the kidneys 445. The ultrasonic transducer 180 may be placed against the interior wall of the stomach closest to a blood vessel leading to one of the kidneys 445 (for example, the right renal 510 or the left renal 435) to obtain necessary imaging through minimally invasive means. Quantity of blood flow may be imaged and/or measured under the present invention thereby allowing early detection of any number of potential risks including, for example, renal artery stenosis, arterial narrowing and kidney failure. Those skilled in the art will recognize that imaging of blood flow may also be useful for a number of applications including, but not limited to, performing minimally invasive heart surgery, Transjugular Intra-Hepatic Porto-Systemic Shunts (TIPS) procedures and fixing aortic aneurysms. The present invention will also permit imaging that will permit intra-arterial stent placement or balloon angioplasty to treat narrowing of the aorta or any branch vessel including the renal arteries and celiac and mesenteric and iliac arteries. The present invention may also be used to locate devices inserted percutaneously or surgically within intra-abdominal arteries or veins such as, for example, the abdominal aorta, the celiac, the superior mesenteric, the left and right renal arteries, the entire length of the vena cava including the retro-hepatic vena cava, portal veins, hepatic veins and renal veins. Further, pre-operative and post-operative imaging of blood vessels in liver transplant patients including the hepatic arteries, portal vein and hepatic veins is made possible under the present invention. Richard R. Keen, James S. T. Yao, Patricia Astleford, Donna Blackburn and Lee J. Frazin, in "Feasibility of Transgastric Ultrasonagraphy of the Abdominal Aorta", J. Vascular Surgery 834–841, V.24, No. 5 (1996) disclose the images that can be obtained of blood vessels where a transducer 180 is adequately positioned to be in contact with the inside wall of the stomach. In that case, however, invasive surgery was required.

The imaging devices 100 and 300 may also be used to when implanting filters in the vena cava to trap blood clots. The imaging devices 100 and 300 provide high resolution images of the vena cava such that implantable filter devices may be properly viewed and accurately positioned within the vena cava thereby eliminating the need for x-rays or radio-opaque intra-venous contrast agents.

In the foregoing specification, the present invention has been described with reference to specific exemplary embodiments thereof. Although the invention has been described in terms of a preferred embodiment, those skilled in the art will recognize that various modifications, embodiments or variations of the invention can be practiced within the spirit and scope of the invention as set forth in the appended claims. All are considered within the sphere, spirit, and scope of the invention. The specification and drawings are, therefore, to be regarded in an illustrated rather than restrictive sense. Accordingly, it is not intended that the invention be limited except as may be necessary in view of the appended claims.

What is claimed is:

1. A device for facilitating ultrasound imaging of internal structures near a stomach of a patient comprising;
   (a) a flexible probe having a bendable head, a bendable body and an end opposite the head;
   (b) an ultrasound transducer disposed on the head of the probe; and
   (c) a substantially rigid sheath made of a material having a resiliency that permits insertion of the sheath within a mouth of the patient, the sheath capable of covering at least a portion of the body of the probe for selectively limiting bending of a portion of the body, whereby the head may be precisely positioned near a wall of the stomach.

2. The system of claim 1, further comprising a handle coupled near the end of the probe to allow manual positioning the ultrasound transducer.

3. The system of claim 1, further comprising a gel material disposed on the ultrasound transducer to enable a proper contact between the ultrasound imaging device and the interior wall portion of the stomach.

4. The system of claim 1, further comprising a liquid material on the ultrasound transducer to enable a proper contact between the ultrasound imaging device and the interior wall portion of the stomach.

5. The system of claim 1, further comprising a protective cover encompassing the probe and the ultrasound transducer to provide a sterile barrier between the ultrasound imaging device and the patient.

6. The system of claim 1, wherein center of the ultrasound transducer is in the range of 1 centimeter to 10 centimeters from end of the sheath.

7. The system of claim 1, wherein the ultrasound transducer is adapted to operate in a Doppler mode of operation to image blood flow within blood vessels.

8. The system of claim 7, wherein the ultrasound transducer operating in the Doppler mode images blood vessels selected from the group consisting of celiac, hepatic, splenic, superior mesenteric, right renal artery, left renal artery, abdominal vena cava, renal veins, abdominal aorta, hepatic vein, portal vein, mesenteric vein, iliac arteries, and iliac veins.

9. The system of claim 1, wherein the ultrasound transducer is adapted to operate in a B-mode of operation to provide high resolution imaging of internal organs near the stomach of the patient.

10. An ultrasound imaging device for viewing internal structures near a stomach of a patient comprising;
    (a) a probe having a head, a body and an end opposite the head;
    (b) an ultrasound transducer disposed on the head of the probe;
    (c) a flexible sheath covering at least a portion of the body of the probe; and
    (d) a substantially rigid rod capable of being placed within the sheath for selectively limiting bending of at least a portion of the body of the probe.

11. The ultrasound imaging device of claim 10, wherein the sheath has a first cavity and a second cavity, wherein the first cavity covers at least a portion of the body of the probe, and wherein the rod is capable of being placed within the second cavity.

12. The ultrasound imaging device of claim 10, wherein the rod is placed within the body of the probe.

13. The ultrasound imaging device of claim 10, further comprising a gel material on the ultrasound transducer to enable a proper contact between the ultrasound imaging device and the interior wall portion of the stomach.

14. The ultrasound imaging device of claim 10, further comprising a liquid material on the ultrasound transducer to enable a proper contact between the ultrasound imaging device and the interior wall portion of the stomach.

15. The ultrasound imaging device of claim 10, further comprising a protective cover encompassing the probe and the ultrasound transducer to provide a sterile barrier between the ultrasound transducer and the patient.

16. The ultrasound imaging device of claim 10, wherein center of the ultrasound transducer is in the range of 1 centimeter to 10 centimeters from end of the sheath.

17. The ultrasound imaging device of claim 10, wherein the ultrasound transducer is adapted to operate in a Doppler mode of operation to image blood flow within blood vessels.

18. The ultrasound imaging device of claim 17, wherein the blood vessels are selected from the group consisting of celiac, hepatic, splenic, superior mesenteric, right renal artery, left renal artery, abdominal vena cava, renal veins, abdominal aorta, hepatic vein, portal vein, mesenteric vein, iliac arteries, and iliac veins.

19. The ultrasound imaging device of claim 10, wherein the ultrasound transducer is adapted to operate in a B-mode of operation to provide high resolution imaging of internal organs near the stomach of the patient.

20. The ultrasound imaging device of claim 10, wherein the internal organ is selected from the group consisting of a kidney, a pancreas and a liver.

21. A method of imaging internal structures near a stomach of a patient using a probe having a head, a body and an end, said head having an ultrasound transducer, at least a portion of said body being covered by a substantially rigid sheath made of a material having a resiliency that permits insertion of the sheath within a mouth of the patient for limiting bending of the body, said method comprising the steps of:
    (a) inserting the probe and the substantially rigid sheath into the mouth of the patient to permit entry of the head of the probe into the stomach of the patient;
    (b) positioning the head of the probe within the stomach to allow the ultrasound transducer to be in contact with an internal wall portion of the stomach; and
    (c) imaging of internal structures near the stomach.

22. The method of claim 21, wherein the step of taking detailed images involves the step of operating the ultrasound transducer is adapted to operate in a Doppler mode to view blood flow within blood vessels.

23. The method of claim 22, wherein the blood vessels are selected from the group consisting of celiac, hepatic, splenic, superior mesenteric, right renal artery, left renal artery, abdominal vena cava, renal veins, abdominal aorta, hepatic vein, portal vein, mesenteric vein, iliac arteries, and iliac veins.

24. The method of claim 21, wherein the step of taking detailed images involves the step of operating the ultrasound transducer is adapted to operate in a B-mode to view an internal organ near the stomach of the body.

25. The method of claim 24, wherein the internal organ is selected from the group consisting of a kidney, a pancreas and a liver.

26. The method of claim 21, wherein the step of taking detailed images includes the step of monitoring blood flow of a blood vessel to a kidney or liver.

27. The method of claim 21, wherein the step of taking detailed images includes the step of monitoring location of a filter in a vena cava or an intra-arterial stent.

28. The method of claim 21, wherein the step of taking detailed images includes the step of locating devices inserted within blood vessels.

29. An ultrasound imaging device for viewing internal structures near a stomach of a patient comprising:
   (a) a probe having a head, a body and an end opposite the head;
   (b) an ultrasound transducer coupled to the head of the probe;
   (c) a sheath covering at least a portion of the body of the probe; and
   (d) a rod for insertion into the sheath for limiting bending of the body of the probe in relation to the head, wherein the rod is flexible at room temperature and substantially rigid near the temperature of the patient's body.

30. A method of imaging internal structures near a stomach of a patient using a probe having a head, a body and an end, said head having an ultrasound transducer, at least a portion of said body being covered by a sheath, said method comprising the steps of:
   (a) inserting the probe and the sheath into a mouth of a patient to permit entry of the head of the probe into the stomach of the patient;
   (b) inserting a rod into the sheath to limit bending of the body of the probe;
   (c) positioning the head of the probe within the stomach to allow the ultrasound transducer to be in contact with an internal wall portion of the stomach; and
   (d) imaging of internal structures near the stomach.

31. The method of claim 30, wherein the rod is substantially rigid.

32. The method of claim 30, wherein the rod is flexible at room temperature and substantially rigid at body temperature.

33. The method of claim 32, wherein the rod is made of nitinol.

34. A method of imaging internal structures near a stomach of a patient using a probe having a head, a body, an end and a cavity, said head having an ultrasound transducer, said method comprising the steps of:
   (a) inserting the probe into a mouth of a patient to permit entry of the head of the probe into the stomach of the patient;
   (b) inserting a rod into the cavity of the probe to limit bending of the body;
   (c) positioning the head of the probe within the stomach to allow the ultrasound transducer to be in contact with an internal wall portion of the stomach; and
   (d) imaging of internal structures near the stomach.

35. The method of claim 34, wherein the rod is substantially rigid.

36. The method of claim 34, wherein the rod is flexible at room temperature and substantially rigid at body temperature.

37. The method of claim 36, wherein the rod is made of nitinol.

38. An ultrasound imaging device for viewing internal structures near the stomach of a patient comprising:
   (a) a probe having a head, a body and an end opposite the head;
   (b) an ultrasound transducer coupled to the head of the probe;
   (c) at least one head cable located at least within the head of the probe for locking the head in a substantially rigid position; and
   (d) at least one body cable located at least within the body of the probe for locking the body in a substantially rigid position.

39. The system of claim 38, further comprising a head switch coupled to the end of the probe and the head cable for tightening the head cable.

40. The system of claim 38, further comprising a body switch coupled to the end of the probe and the body cable for tightening the body cable.

41. The system of claim 38, further comprising a handle coupled near the end of the probe to allow manual positioning the ultrasound transducer.

42. The system of claim 38, further comprising a gel material covering the ultrasound transducer to enable a proper contact between the ultrasound imaging device and the interior wall portion of the stomach.

43. The system of claim 38, further comprising a liquid material covering the ultrasound transducer to enable a proper contact between the ultrasound imaging device and the interior wall portion of the stomach.

44. The system of claim 38, further comprising a protective cover encompassing the probe and the ultrasound transducer to provide a sterile barrier between the ultrasound imaging device and the patient.

45. The system of claim 38, wherein the ultrasound transducer has a Doppler mode of operation to image blood flow within blood vessels.

46. The system of claim 45, wherein the ultrasound transducer operating in the Doppler mode images blood vessels selected from the group consisting of celiac, hepatic, splenic, superior mesenteric, right renal artery, left renal artery, abdominal vena cava, renal veins, abdominal aorta, hepatic vein, portal vein, mesenteric vein, iliac arteries, and iliac veins.

47. The system of claim 38, wherein the ultrasound transducer has a B-mode of operation to provide high resolution imaging of internal organs near the stomach of the patient.

48. A method of imaging internal structures near a stomach of a patient using a probe having a head, a body and an end, said head having an ultrasound transducer, said method comprising the steps of:
   (a) inserting the probe into the a mouth of a patient to permit entry of the head of the probe into the stomach of the patient;
   (b) limiting the bending of at least a portion of the body of the probe;
   (c) positioning the head of the probe within the stomach to allow the ultrasound transducer to be in contact with an internal wall portion of the stomach; and
   (d) imaging of internal structures near the stomach.

* * * * *